(12) United States Patent
Nakamura et al.

(10) Patent No.: US 6,905,501 B2
(45) Date of Patent: Jun. 14, 2005

(54) BONE CONNECTING DEVICE AND METHOD OF MANUFACTURING THE SAME

(75) Inventors: Saburo Nakamura, Ayabe (JP); Morishige Hata, Ayabe (JP); Takashi Nishiyama, Ayabe (JP); Takahiro Yoshioka, Ayabe (JP); Hajime Takeuchi, Ayabe (JP); Toru Yamamoto, Ayabe (JP); Yasuyuki Kishida, Ayabe (JP); Toru Arima, Ayabe (JP)

(73) Assignee: Gunze Limited, Kyoto (JP)

( * ) Notice: Subject to any disclaimer, the term of this patent is extended or adjusted under 35 U.S.C. 154(b) by 388 days.

(21) Appl. No.: 10/299,090

(22) Filed: Nov. 18, 2002

(65) Prior Publication Data

US 2003/0146541 A1 Aug. 7, 2003

Related U.S. Application Data

(63) Continuation of application No. 09/530,152, filed as application No. PCT/JP98/04889 on Apr. 25, 2000.

(30) Foreign Application Priority Data

Oct. 29, 1997 (JP) .............................................. 9-336257
Nov. 6, 1997 (JP) .............................................. 9-343580

(51) Int. Cl.⁷ .......................... B28B 21/92; A61B 17/86
(52) U.S. Cl. ......................... 606/73; 264/293; 264/294

(58) Field of Search ..................... 606/72, 73, 75–77, 606/154; 264/293, 294, 296, 320, 323

(56) References Cited

U.S. PATENT DOCUMENTS

| 2,957,205 A | * | 10/1960 | Barber et al. ............... 264/296 |
| 3,859,409 A | * | 1/1975 | Coonrod ..................... 264/295 |
| 4,224,275 A | * | 9/1980 | Sauer .......................... 264/516 |
| 4,521,356 A | * | 6/1985 | Keller et al. ................. 264/600 |
| 4,863,330 A | | 9/1989 | Olez et al. ................... 411/424 |
| 5,529,736 A | * | 6/1996 | Shalaby et al. ............. 264/162 |

FOREIGN PATENT DOCUMENTS

| DE | 4308239 | 6/1994 |
| EP | 0795336 | 9/1997 |
| JP | 63901 | 3/1991 |
| JP | 469846 | 11/1992 |
| JP | 4314508 | 11/1992 |
| JP | 168647 | 7/1993 |
| JP | 116922 | 5/1996 |
| JP | 9266918 | 10/1997 |

* cited by examiner

Primary Examiner—David O. Reip
(74) Attorney, Agent, or Firm—Baker Botts LLP

(57) ABSTRACT

The present invention provides a method for producing a bone joining device having a head portion, the method comprising the step of press-molding a (primary) molded article to form a head portion, and a bone joining device having a head portion, wherein the molecular orientation in the (primary) molded article is substantially maintained.

1 Claim, 6 Drawing Sheets

Orientation in cut screw (image)

Orientation in pressed screw (image)

BONE CONNECTING DEVICE AND METHOD OF MANUFACTURING THE SAME

CROSS-REFERENCE TO RELATED APPLICATIONS

This application is a continuation of U.S. patent application Ser. No. 09/530,152, filed Apr. 25, 2000, which is a national phase application of International Application No. PCT/JP98/04889, which was filed on Oct. 29, 1998 and which published in Japanese on May 6, 1999, which in turn claims priority from Japanese Application No. 336257/1997, which was filed non Oct. 29, 1997, and from Japanese Application No. 343580/1997, which was filed on Nov. 6, 1997.

TECHNICAL FIELD

The present invention relates to a bone joining device used for joining and fixing fractured or damaged bones, and a method for producing the same.

BACKGROUND ART

In recent years, polylactic acid, polyglycolic acid, a copolymer of polylactic acid and polyglycolic acid and like biodegradable and bioabsorbable polymers are applied to bone joining devices as substitute material for metals, ceramics etc. since there is no need to remove the bone joining material after operation.

These bone joining devices are produced using fusion-molded articles which are formed, usually by cutting, into various shapes such as screws, nails, pins, tapping screws, plates, bolts, rivets, staples, washers, anchors, wires, etc.

However, the above method requires an advanced cutting technique and considerable time. When the molded articles are stretched products having improved flexural strength and tensile strength, formed fibrils or oriented molecules are cut by the cutting operation, thereby causing the problems of lowered strength and accelerated degradation rate of the articles. Furthermore, the head portion of the above bone joining devices usually has a larger diameter than its shank portion. Therefore, it has been problematic that a great amount of cut dust is produced by cutting a molded article having the diameter of the head portion to form the narrower shank portion.

Further, the bone joining devices, in case of a screw, have a drawback of impaired screw thread strength since fibrils or oriented molecules therein are cut.

In view of eliminating the above drawbacks of the prior art, an object of the present invention is to provide a bone joining device which can be produced with improved productivity in a higher yield.

Another object of the present invention is to provide a method for producing a novel bone joining device having screw threads with greatly improved shear strength, particularly a method for producing a screw-like product.

DISCLOSURE OF THE INVENTION

Figure 1:
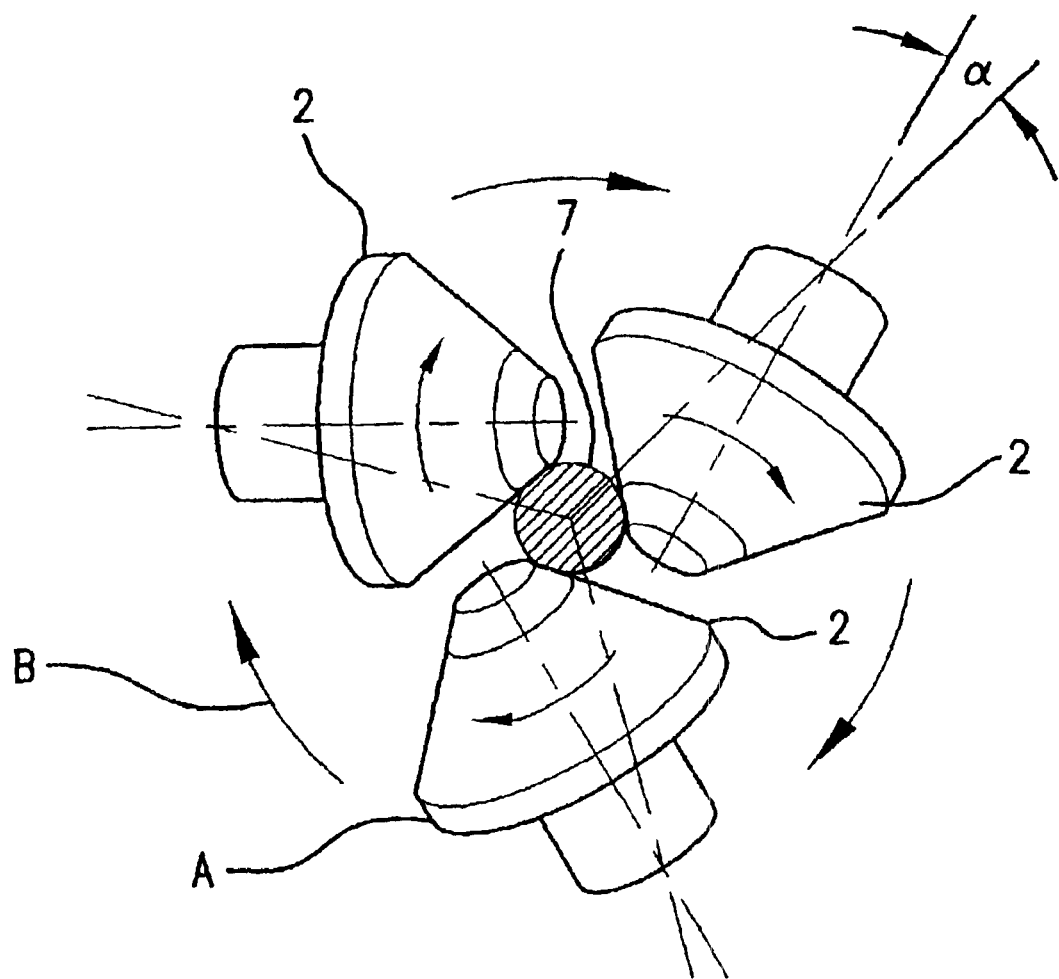
FIG. 1 is a front view showing an example of the stretching process of the molded article for use in the invention.

The present invention provides the following bone joining device and a method for producing the same.

Item 1. A method for producing a bone joining device having a head portion, the method comprising a step of forming a head portion by press-molding a primary molded article.

Item 2. The method for producing a bone joining device according to item 1, wherein the press molding is carried out from the axial direction of the molded article.

Item 3. The method for producing a bone joining device according to item 1, wherein the (primary) molded article comprises a biodegradable and bioabsorbable polymer.

Item 4. The method for producing a bone joining device according to item 1, wherein the bone joining device is a screw-like product, the method comprising the steps of forming a screw head portion having a larger diameter than a shank portion thereof by pressing the molded article comprising a biodegradable and bioabsorbable polymer from the axial direction of the molded article; and forming ridges and grooves by pressing the molded article from the direction perpendicular to the axis of the molded article.

Item 5. The method for producing a bone joining device according to item 4, wherein the screw head portion is formed by pressing with an upsetting punch.

Item 6. The method for producing a bone joining device according to item 5, wherein the screw head portion is simultaneously formed by pressing with an upsetting punch having grooves for screwing.

Item 7. The method for producing a bone joining device according to item 4, wherein thread grooves are formed by pressing with a multi-piece mold having thread grooves.

Item 8. The method for producing a bone joining device according to item 7, wherein a four-piece mold is used.

Item 9. The method for producing a bone joining device according to item 1, wherein thread grooves are formed by pressing with a multi-piece mold having thread grooves, the method characterized in that pressing is carried out at least twice; and that the second and the following pressing are carried out in such a manner that the joining portions of the mold fall on other parts of the molded article than those formed by the previous pressing.

Item 10. The method for producing a bone joining device according to item 4, wherein the molded article comprising a biodegradable and bioabsorbable polymer is subjected to a stretching process so as to impart orientation.

Item 11. The method for producing a bone joining device according to item 10, wherein the molded article is stretched in the longitudinal direction thereof.

Item 12. A bone joining device having a head portion in which the orientation in the (primary) molded article is substantially maintained.

Item 13. The bone joining device according to item 12, wherein the bone joining device having a head portion is a screw, nail, pin, tapping screw, bolt, rivet or like products.

Item 14. The bone joining device according to item 13 which is obtainable by press-molding the (primary) molded article from the axial direction of the axis thereof.

Item 15. The bone joining device according to item 14, wherein press molding is carried out using an upsetting punch.

Item 16. The bone joining device according to item 13 which further has grooves for screwing in which the orientation in the (primary) molded article is substantially maintained.

Item 17. The bone joining device according to item 12 comprising a biodegradable and bioabsorbable polymer.

The biodegradable and bioabsorbable polymer for use in the present invention may be suitably selected from those mentioned in the above, i.e., polylactic acid (L form; D form; a polymer blend, copolymer or stereo complex of L form and D form) polyglycolic acid, a copolymer of lactic acid and glycolic acid, a copolymer of lactic acid and caprolactone having a molecular weight of tens of thousands to about one million, and said polymers further containing hydroxyapatite, A-W crystallized glass, alumina, zirconia, calcium phosphate, carbon, bioglass and like bioceramics. However, useful polymers are not limited to those mentioned in the above and include other thermoplastic biodegradable and bioabsorbable polymer.

A (primary) molded article comprises a polymer material such as a biodegradable and bioabsorbable polymer. The (primary) molded article can be produced, for example, by fusing polymer chips and extruding into any desired shape such as a rod and plate; pressing to produce a molded article or further stretching the same in the longitudinal direction thereof with heating as disclosed in Japanese Examined Patent Publication No. 63901/1991; by extrusion stretching with the application of pressure and heat by means of a heating medium (hydrostatic pressure extrusion) through a nozzle as disclosed in Japanese Unexamined Patent Publication No. 168647/1993; or rolling by passing between a plurality of rotating planetary slant rolls with heating as mentioned in Japanese Patent Application No. 116922/1996. Preferable methods are those which are capable of providing molecular orientation and improving strength of the product.

"A screw-like product" may be the products having ribs and grooves, for instance, screws and pins. The ribs and grooves formed on the screw-like products, in case of screws and pins, correspond to thread groove (spiral groove) and ribs and grooves, respectively.

Press molding is conducted at a temperature not lower than the glass transition temperature but not higher than the melting point of the molded article and at a pressure of 100–500 kg/cm$^2$ so that the molded article undergoes at least plastic deformation. To maintain the shape of the molded article after orientation and pressing, the preferable temperature during press molding is, for example, about 100–130° C. in case of poly-L-lactide (PLLA).

In the present invention, "the molecule orientation in a (primary) molded article is substantially maintained" means that the oriented polymer molecules existing on the surface of the molded article are completely uncut or substantially uncut unlike in a cutting process. Whether or not the polymer molecules have been cut can be determined, for example, by observation with an electron microscope or conducting a thread rib breaking test to observe the cut surface of the molded article.

The bone joining screw produced by the method of the invention, particularly when pressed at least twice, is favorable because they are substantially free of burrs (projections).

The viscosity-average molecular weight of the biodegradable polymer varies depending on the application of the bone joining device and the type of the biodegradable polymer. In case of PLLA, for example, the viscosity-average molecular weight is about 50,000–1,000,000, preferably about 50,000–600,000.

The tensile strength of the bone joining device is, for example, at least 80%, preferably not lower than 90% of its initial strength after being immersed in a phosphate buffer at 37° C. for three months.

BEST MODE FOR CARRYING OUT THE INVENTION

The present invention will be described below in detail with examples.

EXAMPLE 1

FIG. 1 shows planetary slant rolls in which a molded article 1 is passed between three rollers 2 spinning in the direction A and revolving in an orbit in the direction B with heating and pressure and rolled. The resulting molded article has a helical orientation in the spinning and revolving directions of the rollers. Therefore, it is preferable to provide thread grooves in a direction accelerating the helical orientation, i.e., in a manner of conforming the helical direction to the thread groove direction so that the screwing strength is further improved.

Figure 2A:
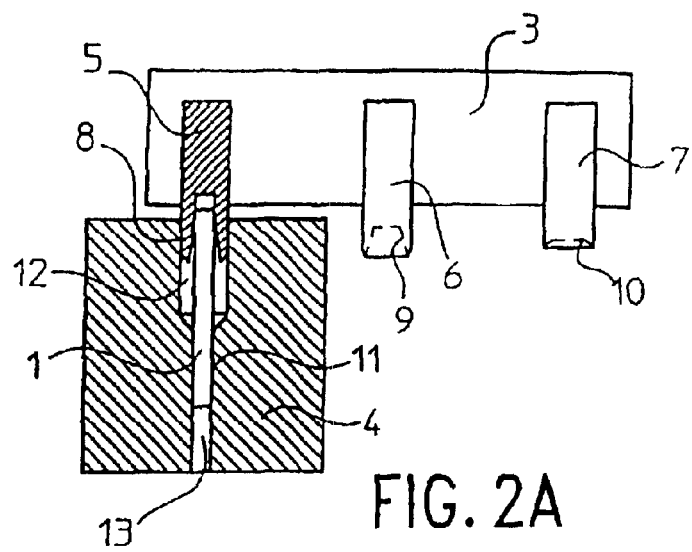
FIG. 2 is an operation chart showing an example of the method for producing the screw head portion of the invention.
Figure 2B:
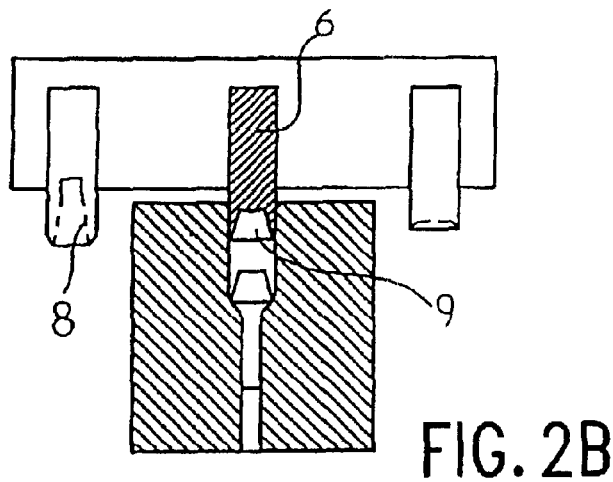
Figure 2C:
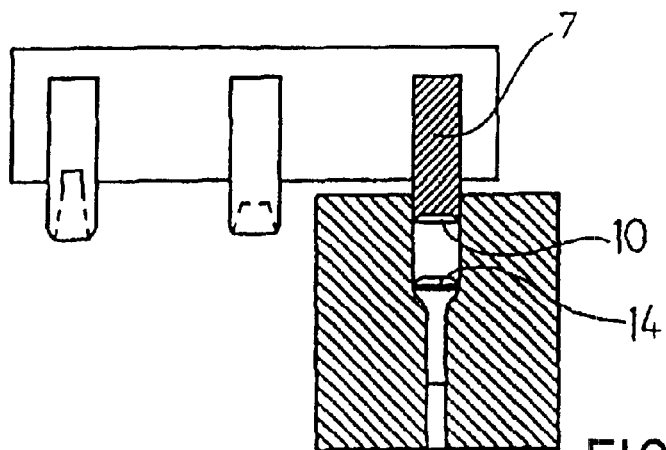

FIG. 2 shows an example of the molding device to form a head portion of a screw which is taken as an example of the bone joining device having a head portion.

Figure 3:
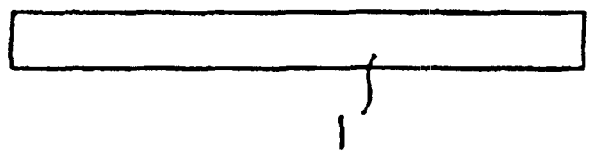
FIG. 3 is a side view showing the change in configurations of the screw head portion formed in the process of FIG. 2.
Figure 3A:
Figure 3B:
Figure 3C:
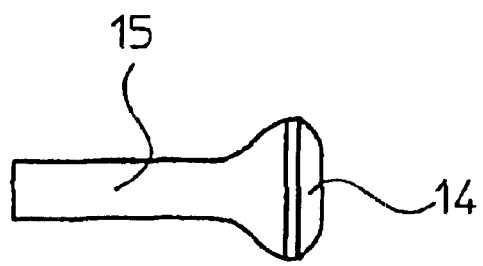

By the processes shown in (A)–(C) of FIG. 2, the screw head portions having the shapes shown in (A)–(C) of FIG. 3 are formed.

The device for forming the screw head portion comprises a press device 3 equipped with three upsetting punches 5, 6, 7 fixedly mounted thereon, and a mold 4 which accepts a molded article. The first upsetting punch 5 is provided with a long cavity 8 having an approximate trapezoidal shape; the second upsetting punch 6 is provided with a cavity 9 having a trapezoidal shape and being shorter in length but wider in diameter than the cavity 8; and the third upsetting punch 7 is provided with a cavity 10 having the same size and shape as those of the desired screw head portion. The mold 4 is equipped with a cylindrical portion 11 which accepts a cylindrical molded article 1 to be molded and has the diameter similar to that of the cylindrical molded article, and a cylindrical portion 12 which has a larger diameter and admits the upsetting punch therein to form the screw head portion.

In the above device, a first pressing process is carried out as shown at (A) in FIG. 2. Firstly, a long molded article 1 produced by molding a biodegradable and bioabsorbable resin (e.g., poly-L-lactic acid) into a cylindrical shape is inserted into the cylindrical portion 11 having a smaller diameter. After fixing the end of the molded article 1 by a stopper 13, heated first upsetting punch 5 is operated to pressurize the end of the molded article 1 from the axial direction of the molded article for a certain period of time. The molded article is drawn out therefrom after being cooled.

Subsequently, the second and third upsetting punches 6 and 7 are heated and operated in the order shown at (B) and (C) in FIG. 2. The molded article is then cooled, finally giving the desired screw head portion. The formed screw head portion changes its shape in the order shown at (A)–(C) in FIG. 3. That is, the screw head portion is given the shape shown at (A) in FIG. 3 in the step (A) in FIG. 2; the shape shown at (B) in FIG. 3 in the step (B) in FIG. 2; and the shape shown at (C) in FIG. 3 in the step (C) in FIG. 2.

In Example 1, the step (C) in FIG. 2 is finally conducted, thereby forming a screw head portion 14 having the size and shape shown at (C) in FIG. 3.

At (C) in FIG. 3, 15 represents a shank portion. The shank portion is, for example, pressed with a mold having thread grooves, or threaded by cutting with a lathe. The processing of the shank portion, i.e., the formation of the thread grooves, may be carried out before or after forming the screw head portion.

In addition, the shank portion 15 may be left unthreaded, and may take any shape such as a rivet, pointed nail or pin having ribs and grooves for preventing slippage thereon. The number of the above upsetting punches, the shape and size of the cavities, the formation of the fitting slits such as a cross-shaped, straight and square-shaped slits that fit one end of the screwdriver are optional. The fitting slit can be formed, for example, by providing a ridge corresponding with the cross-shaped slit or straight slit inside the cavity of the upsetting punch during the pressurizing process as mentioned in the above.

In the molding process, conditions and means for pressurizing are not limited. However, it is preferable that the upsetting punch or mold is heated at a temperature not lower than the glass transition temperature but not higher than the melting point of the molded article so that the molded article undergoes at least plastic deformation. It is also preferred that a cooling process is suitably provided in order to set the shape of the molded article.

In the foregoing example, the mold 4 is preferably dividable so that the product is easily drawn out.

At (C) in FIG. 3, 15 represents a portion in which the thread grooves mentioned in the following are formed.

Figure 4A:
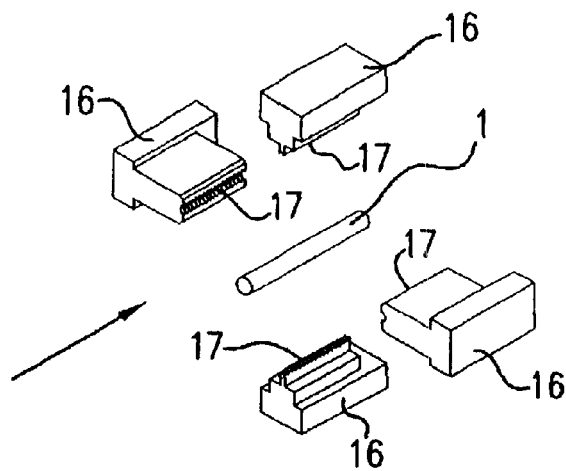
FIG. 4 is an operation chart showing an example of the production of thread grooves of the invention.

Thus, in FIG. 4, 16 are the molds which are uniformly divided into four portions. The molds have thread grooves 17 which are divided into four portions. These divided molds form a mold having a complete set of thread grooves when joined together.

Figure 4B:
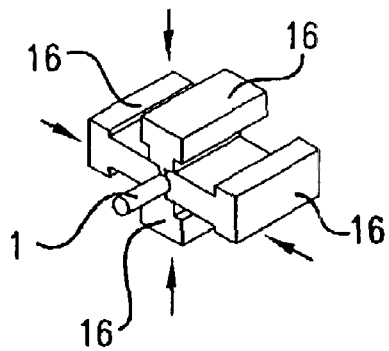
Figure 4C:
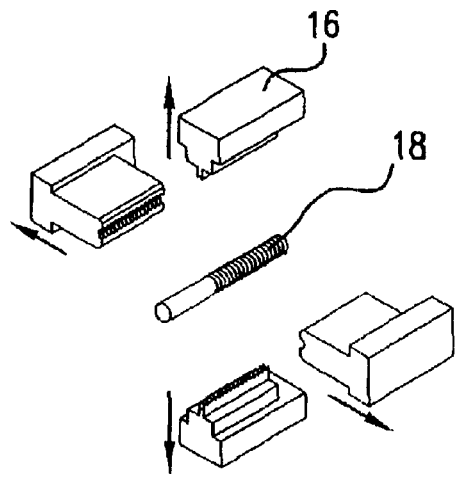

Meanwhile, 1 represents a molded article produced by molding a biodegradable and bioabsorbable resin into a cylinder. As shown in FIG. 4(B), this article is pressurized by each of the molds 16 from four directions, i.e., from the directions perpendicular to the axis of the molded article for a certain period of time, followed by cooling in this state. Subsequently, as shown in FIG. 4(C), the molds 16 are released, forming thread grooves 18 on the molded article 1. Preferably, the resulting molded article is turned 45° and further pressurized in a manner shown at (B) in FIG. 4 to remove the burrs (projections) at the joining portions produced by the first pressurizing between the joined molds. By repeating this operation, the burrs are completely removed. The heating temperature of the molds in this operation is preferably set lower than in the first pressurizing operation, for example, at a temperature slightly higher than the glass transition temperature of the molded article.

The shape and size of the screw formed on the mold may be as desired, and the mold is preferably a four-piece mold. This is because it is difficult for a two-piece mold to draw out the molded article therefrom; a three-piece mold causes a large amount of overflowing resin from the joining portion of the mold; and molds having more than four pieces are disadvantageous to the four-piece mold in their production cost and accuracy.

The heating temperature of the mold may be the temperature at which the molded article undergoes plastic deformation, as mentioned in the above. The heating period, although varying depending on the heating temperature, may be from about several tens of seconds. A cooling means for setting the form of the molded article may be air cooling or water cooling.

The molded article 1 to be molded at the above conditions has a cylindrical shape. The diameter of the molded article 1 is preferably such that the volume of the thread ridges and thread grooves formed thereon are equal.

The molded article may be stretched or unstretched. However, it is preferably stretched along its long axis, i.e., in the above example, in the longitudinally direction thereof. In this manner, the molded article is pressurized perpendicularly to the stretched direction thereof, and fibrils or oriented molecules remain uncut and twisted unlike by cutting process, forming highly strengthened thread grooves.

Although FIG. 4 shows a screw without a screw head portion, a screw having a screw head portion formed by the above-mentioned method may be used. The screw head portion may be molded according to the above method after forming thread grooves.

The present invention can be readily produced; is suitable for mass production; and does not require a special technique such as cutting process. Therefore, it is free from quality variation and material loss resulting from the cutting operation.

Conventionally, when forming the screw head portion larger in diameter than the thread grooves as in the present invention, a molded article having the same diameter as the screw head portion is cut to form thread grooves of a smaller diameter, whereby a large amount of cut dust is produced, resulting in loss of the expensive material. This problem can be solved in the method of the present invention.

In forming thread grooves, more accurate thread grooves can be formed by using a multi-piece mold. Burr occurrence due to the multi-piece mold can be prevented by pressurizing with the mold from different angles for a few times.

In addition, the molded article to be processed in the method of the present invention may be an unstretched article or a stretched article for strength improvement. However, decrease in its strength can be prevented particularly when a stretched molded article is used as a raw material because it facilitates the processing and fibrils or oriented molecules caused by stretching are left uncut.

The method of this stretching process is not restricted. However, when the bone joining device is a screw, the molded article which is processed in such a manner that the molded article is given a twist orientation is particularly effective when applied by screwing.

Moreover, the method of the invention is also applicable in the production of the bone joining devices resembling screws in their configurations, such as nails or pins.

TEST EXAMPLE 1

PLLA (viscosity average molecular weight: 100,000) was pelletized with a palletizer. The pellets were fed to an extruder with heating at 200° C., fused and mixed in the extruder. The molten product was extruded, giving a cylindrical molded article.

The resulting molded article is stretched 2.5 times its original length by a hydrostatic extruder filled with glycerin at 140° C. at the extrusion rate of 45 mm/min, giving a stretched molded article having a diameter of 3.7 mm. The stretched molded article is processed by a molding apparatus shown in FIG. 2 to form a screw head portion thereon, and then thread grooves are formed with a mold shown in FIG. 4, giving three screws of the invention (sample No. 1–3).

The molded article produced by hydrostatic extrusion is cut into three screws of conventional type (sample No. 4–6).

Figure 7:
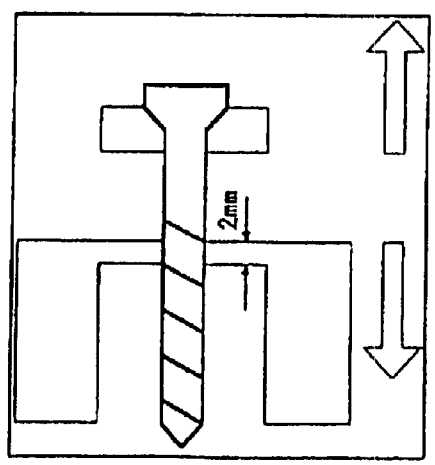
FIG. 7 is a drawing which shows the method of the shear strength test in Test Example 1.

The crest diameter, root diameter, rupture strength, shearing area and shear strength of the obtained samples No. 1–6 are shown in Tables 1 and 2. It can be seen that the pressed products of the present invention are about 1.6 times as high as the conventional cut products in shear strength (screw strength). The shear strength was determined according to JIS Z2241 (metal screw tensile test), i.e., the test method shown in FIG. 7 under the following conditions.

| Tensile testing machine: | Shimazu AUTOGRAPH AGS-5kNG |
|---|---|
| Load cell: | Shimazu SBL-5kN (500 kgf) |
| Elastic stress rate: | 5 mm/min. |

TABLE 1

| Sample No. | Crest diameter $\phi$ D (mm) | Root diameter $\phi$ D1 (mm) | Rupture strength (kgf) | Shearing area (mm$^2$) | Shear strength (kgf/mm$^2$) |
|---|---|---|---|---|---|
| 1 | 4.48 | 3.35 | 61.07 | 7.44 | 8.21 |
| 2 | 4.35 | 3.35 | 59.00 | 6.34 | 9.31 |
| 3 | 4.24 | 3.26 | 56.38 | 5.52 | 10.21 |
| Average | 4.36 | 3.32 | 58.82 | 6.43 | 9.24 |

TABLE 2

| Sample No. | Crest diameter $\phi$ D (mm) | Root diameter $\phi$ D1 (mm) | Rupture strength (kgf) | Shearing area (mm$^2$) | Shear strength (kgf/mm$^2$) |
|---|---|---|---|---|---|
| 4 | 4.46 | 3.26 | 44.67 | 7.44 | 6.00 |
| 5 | 4.45 | 3.26 | 42.33 | 7.44 | 5.69 |
| 6 | 4.46 | 3.27 | 44.18 | 7.44 | 5.94 |
| Average | 4.46 | 3.26 | 43.73 | 7.44 | 5.88 |

TEST EXAMPLE 2

Three pressed screws (sample No. 7–9) of the invention obtained from the same lot as Test Example 1 and three conventional cut screws (sample No. 10–12) were selected.

These screws were immersed in a phosphate buffer at 37° C. for 7 months. The tensile strength of the samples (No. 7–12) was determined after 0 month before immersion, 3 months and 6 months. The results are shown in FIG. 5.

Figure 5:
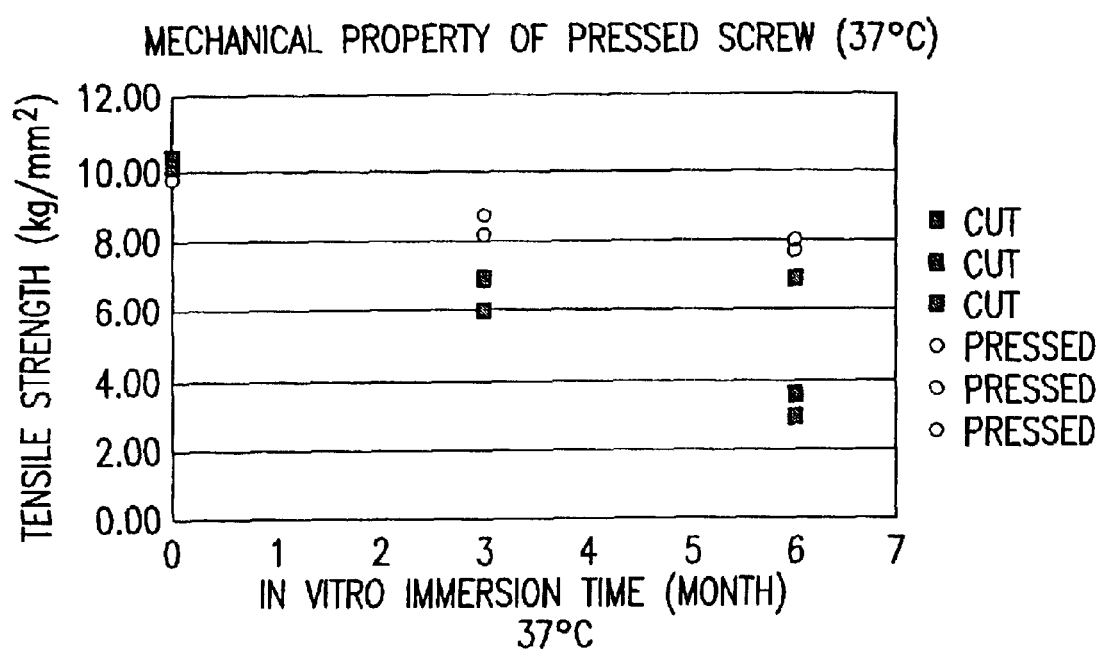
FIG. 5 is a drawing which shows the tensile strength of the pressed screw of the invention and a cut screw as a control sample when immersed in a phosphate buffer at 37° C.
Figure 6A:
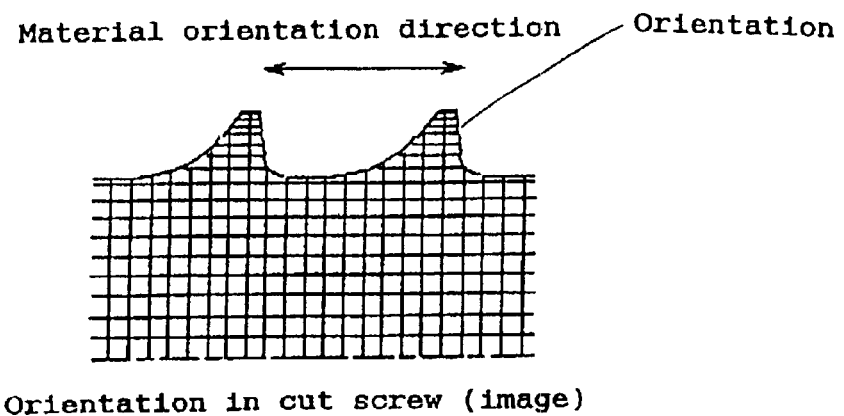
FIG. 6 is a drawing which shows images of the orientation in the pressed screw of the invention and a cut screw as a control sample.
Figure 6B:
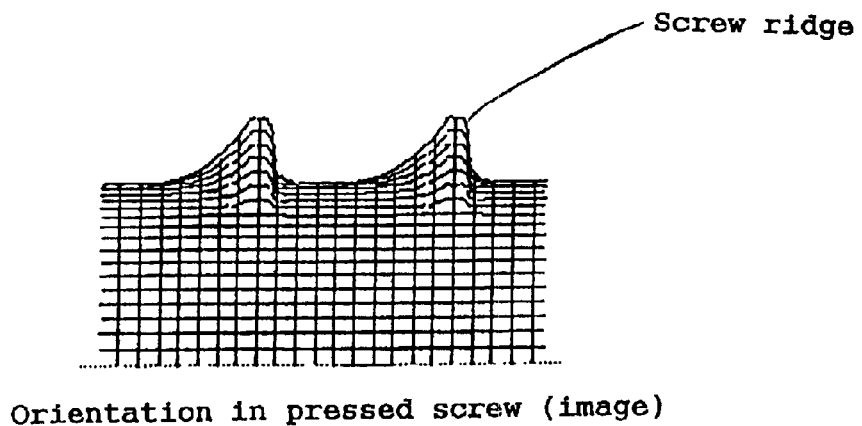

FIG. 5 shows that the pressed molded article of the present invention has a more moderate lowering rate of the tensile strength than the cut products, and therefore is suitable for a bone joining device which needs to retain its high strength for a long period of time.

We claim:

1. A method for producing a bone joining device having a head portion, the method comprising a step of forming a head portion by press-molding a molded article which comprises a biodegradable and bioabsorbable polymer, wherein thread grooves are formed by pressing with a multi-piece mold having thread grooves and joining portions, wherein the method comprises a first pressing and at least one additional pressing, wherein each of the at least one additional pressing follows a previous pressing and is carried out in such a manner that the joining portions of the mold fall on other parts of the molded article than those formed by the previous pressing.

* * * * *